US005739108A

United States Patent [19]

Mitchell

[11] Patent Number: 5,739,108
[45] Date of Patent: *Apr. 14, 1998

[54] PROLONGED RELEASE OF BIOLOGICALLY ACTIVE POLYPEPTIDES

[75] Inventor: James W. Mitchell, St. Louis, Mo.

[73] Assignee: Monsanto Company, St. Louis, Mo.

[*] Notice: The term of this patent shall not extend beyond the expiration date of Pat. Nos. 5,086,041, 5,411,951 and 5,474,980.

[21] Appl. No.: 570,304

[22] Filed: Dec. 11, 1995

Related U.S. Application Data

[60] Continuation of Ser. No. 900,410, Jun. 18, 1992, Pat. No. 5,474,980, which is a division of Ser. No. 568,284, Aug. 16, 1990, abandoned, which is a division of Ser. No. 414,503, Sep. 29, 1989, Pat. No. 5,013,713, which is a continuation of Ser. No. 787,873, Oct. 16, 1989, abandoned, which is a continuation-in-part of Ser. No. 657,713, Oct. 4, 1984, abandoned.

[51] Int. Cl.⁶ .......................... A61K 38/27; C07K 14/61
[52] U.S. Cl. ............................................. 514/12; 530/399
[58] Field of Search .............................. 514/12; 530/399

[56] References Cited

U.S. PATENT DOCUMENTS

| 3,869,549 | 3/1975 | Geller | 424/177 |
| 4,659,696 | 4/1987 | Hirai et al. | 514/15 |
| 5,013,713 | 5/1991 | Mitchell | 514/2 |
| 5,086,041 | 2/1992 | Mitchell | 514/12 |
| 5,411,951 | 5/1995 | Mitchell | 514/12 |
| 5,474,980 | 12/1995 | Mitchell | 514/12 |

OTHER PUBLICATIONS

Davis et al. "Continuous Elevation of Blood Growth Hormone Concentrations by Beeswax Implant", J. Dairy Science 66: 1980–1982.

Primary Examiner—Cecilia J. Tsang
Assistant Examiner—Anish Gupta
Attorney, Agent, or Firm—Gary M. Bond

[57] ABSTRACT

Prolonged parenteral release of a bioactive polypeptide at desirably effective levels can be achieved using novel compositions in which the polypeptide is present in a biocompatible oil in an unusually high proportion such as at least about 10% by weight. Also disclosed are certain metal-associated somatotropins that are useful for prolonged parenteral release of such somatotropins.

9 Claims, No Drawings

PROLONGED RELEASE OF BIOLOGICALLY ACTIVE POLYPEPTIDES

This application is a continuation of U.S. Ser. No. 07/900,410, filed Jun. 18, 1992, now issued as U.S. Pat. No. 5,474,980, which was a Divisional of U.S. Ser. No. 07/568,284, filed Aug. 16, 1990, now abandoned, which was a Divisional of U.S. Ser. No. 07/414,503, filed Sep. 29, 1989, now issued as U.S. Pat. No. 5,013,713 which was a Continuation of U.S. Ser. No. 06/787,873, filed Oct. 16, 1985, now abandoned which was a Continuation-In-Part of U.S. Ser. No. 06/657,713 filed Oct. 4, 1984 now abandoned.

This invention relates to biologically active polypeptide compositions which can be parenterally administered for prolonged release in animals, to methods of using such compositions, to metal-associated somatotropins useful in certain of such compositions, and to processes for preparing such metal-associated somatotropins.

BACKGROUND OF THE INVENTION

Although prolonged activity of some biologically active (bioactive) polypeptides can be achieved by parenterally administering only very small doses, others are required in sufficient serum concentrations and/or have such a short half-life in serum that a substantial dose (e.g. at least about 100 mg) must be administered to provide the desired biological effect over an extended time such as a week or longer. Somatotropins (growth hormones) are an example of such polypeptides.

To prevent undesirably rapid release into an animal's bloodstream, certain polypeptides have been parenterally administered in liquid vehicles which may optionally contain hydration retardants (antihydration agents) or in association with metals or metal compounds that further lower their solubility in body fluids. To avoid the need for unacceptably large quantities of such a vehicle, substantial concentrations of the polypeptide in the vehicle would be advantageous. However, most bioactive polypeptides are very viscous in substantial concentrations and consequently difficult to inject or otherwise administer in such concentrations. Moreover, many commonly used antihydration agents add viscosity and can diminish convenient injectability of such compositions. For those and other reasons, the right combination of (1) a fast enough release to provide the desired biological effect in the animal, (2) a slow enough release to sufficiently prolong the effect, (3) a dose adequate for release at the required rate over the prolonged period of time and (4) a volume small enough and viscosity low enough for convenient administration has normally been very difficult to achieve.

Since each polypeptide is different, e.g. in its three-dimensional structure and its interaction with other substances, the feasibility of achieving a prolonged effective release with a high loading of polypeptide in a suitable vehicle is impossible to predict or demonstrate theoretically. Yet in many cases, such prolonged release compositions must be developed if the biological activity of the polypeptide is to be provided in a useful, economical fashion.

DISCUSSION OF PRIOR ART

Methods to achieve prolonged release of bioactive substances have been long sought after to reduce frequency of treatments and/or minimize trauma to the treated animal. Prolonged release has been achieved for a number of such substances in various ways. One system is the use of oil solutions which can be injected intramuscularly, subcutaneously or otherwise. In some cases substances of lower oil solubility have been administered in oil suspensions.

For example, Welch in U.S. Pat. No. 2,491,537 discloses release up to 24 hours for penicillin suspended in oil (e.g. vegetable) gelled with pectin, a cellulose compound, or a protein such as gelatin. He also suggests extended release for insulin and steroid hormones. Buckwalter in U.S. Pat. 2,507,193 discloses release in rabbits for up to eleven days using 300,000 units/ml of procaine penicillin suspended in peanut oil gelled with 5% aluminum monostearate (AlMS). Jacobson in U.S. Pat. No. 3,016,330 discloses AlMS-coated penicillin suspended in sesame oil. Chien at 35(3) *Journal of Parenteral Science and Technology* 109 (1981) discusses prolonged bioavailability of penicillin G procaine suspended in vegetable oil gelled with 2% AlMS, stating that more than 2% AlMS appears to have only limited benefit for prolonging effective penicillin levels and that suspensions containing more than 2% AlMS are too viscous for practical use.

Oil suspensions have been also utilized for certain low molecular weight (MW) therapeutic substances other than penicillin. For instance, Lachman et al in U.S. Pat. No. 3,676,557 discloses long-acting formulations of up to 50% pamoate salts of normorphinones in oil suspensions gelled with AlMS. Sieger et al in U.S. Pat. No. 4,016,273 discloses prolonged-release formulations of up to 40% pamoate salts of oxazepines in oils gelled with aluminum stearates.

Systems for prolonged release of certain bioactive polypeptides have also been disclosed. For instance, Anschel in U.S. Pat. No. 2,964,448 discloses suspensions of relaxin (about 2%) in a vegetable oil gelled with AlMS. Anschel indicates such a suspension provides relaxation comparable to that in oil without gelling agent (e.g. 5–7 days) and discloses a longer effect (up to 23 days) by heat treating the suspension containing AlMS.

Geller in U.S. Pat. No. 3,869,549 discloses injectable prolonged-release compositions containing "extremely small doses", e.g. "fractions of a milligram" of a peptide. Although growth hormones are mentioned, specific examples are of water soluble corticotrophin (ACTH) preparations active for 7–8 days. In particular, Geller discloses compositions containing acid addition salts of ACTH analogs suspended in groundnut oil gelled with aluminum distearate (AlDS) or adsorbed on AlDS subsequently dispersed in such oil. In either case the analog is in Geller's injectable formulations in concentrations of only 0.03–0.1% and weight ratios of peptide to the aluminum salt no greater than 0.5.

Compositions for extended release of analogs of LH-RH hormone are disclosed by Nestor et al in U.S. Pat. No. 4,256,737. Those compositions contain salts of the hormone, including polyvalent metal (e.g. zinc) salts, in vegetable oil gelled with aluminum salts of fatty acids. The LH-RH analogs are administered at concentrations of 0.01–1% in the injected composition.

Others have disclosed aqueous suspensions of metal salts or complexes of polypeptides for prolonged parenteral release. For instance, Donini in U.S. Pat. No. 3,852,422 discloses long-active aqueous suspensions of a precipitation product of water-soluble gonadotropins and aluminum or zinc hydroxide. Because zinc is naturally present in pancreatic insulin, prolongation of insulin release from aqueous suspensions due to interaction between insulin and various metals (e.g. zinc, nickel, cobalt and cadmium) has been investigated. See U.S. Pat. Nos. 2,143,590; 2,174,862; 2,882,203; 2,920,014 and 3,102,077.

OBJECTS OF THE INVENTION

An object of this invention is to provide compositions which are useful for prolonged release of a biologically active polypeptide in an animal and which are composed of constituents that are biologically compatible with that animal.

Another object is to provide such compositions having a fast enough release to result in the desired biological effect in the animal.

Another object is to provide such compositions having a slow enough release to sustain the desired biological effect for an advantageously prolonged duration.

Another object is to provide such compositions containing a sufficiently high loading (adequate dose) of the polypeptide to sustain the required rate of release over such a prolonged period of time.

Another object is to provide such compositions having a low enough volume for convenient parenteral administration. This is especially important when the dose of polypeptide to be administered is necessarily large.

Another object is to provide such compositions having constituents and their proportions selected such that the compositions have low enough viscosity for convenient injection or other administration. This is also highly important when injection of a relatively large dose of the polypeptide is required.

In some embodiments it is an object that such constituents and their proportions provide a high enough viscosity to assist formation in the animal of depots favoring longer release. In many cases this is difficult to achieve together with the just-mentioned low viscosity objective.

Other objects of the invention include the provision of methods for use of such compositions, certain forms of somatotropins that are advantageously included in such compositions, and processes for preparing such somatotropins. These and other objects of the invention will be more readily apparent from the following detailed description.

SUMMARY OF THE INVENTION

I have discovered that the foregoing objectives can be realized with substantially non-aqueous compositions containing a relatively high proportion of the bioactive polypeptide dispersed in a biocompatible oil sufficient in amount to form a continuous phase of the composition. In many embodiments, such objectives can be more advantageously realized by using polypeptides associated with a non-toxic metal. Optionally, such compositions can include an antihydration agent to further prolong release of the polypeptide. Especially for polypeptides which must be administered in relatively large doses and/or which increase viscosity of the composition substantially, I have found that a relatively high ratio of polypeptide to the antihydration agent is generally advantageous. I have also discovered that compositions can be provided with high loadings of polypeptide (optionally with an antihydration agent) and sufficient viscosity that the compositions, after injection, tend to form into long-lasting depots from which the polypeptide is released in a prolonged manner at an effective rate.

DETAILED DESCRIPTION OF THE INVENTION throughout this specification, percentages of compositions are by weight and temperatures are in degrees Celsius unless indicated otherwise.

As used in this specification and the appended claims, the term "substantially non-aqueous" means essentially anhydrous or containing water in such low proportion that it does not intolerably accelerate release of the polypeptide in the animal. Although this proportion of water varies with each composition of the invention, it is most commonly less than about 2% (even more typically less than about 1%) in a form having such an effect on the polypeptide release.

The term "non-toxic" refers herein to components of compositions of this invention that are reasonably safe and/or innocuous when used in appropriate amounts and under appropriate conditions in parenteral administration of such compositions.

The term "biologically active" or "bioactive" polypeptide herein means a polypeptide that, following appropriate parenteral administration to an animal, has a demonstrable effect on a biological process of that animal. The effect may be hormonal, nutritive, therapeutic, prophylactic or otherwise, and may mimic, complement or inhibit a naturally occurring biological process. Although there is an enormous variety of such effects and processes, the stimulation of growth, lactation, egg or offspring production and/or feed efficiency in food animals can be mentioned as exemplary. Other examples include the production of wool, furs or other non-food animal products. Although polypeptides of smaller MW (e.g. at least about 300) can be used, these polypeptides are generally of substantial MW, e.g. at least about 1000, usually at least about 4000, in most preferred embodiments at least about 9000, and in many even more preferred embodiments at least about 18,000 up to about 30,000 or higher. Although the polypeptide may be in its active form in compositions of this invention prior to administration to an animal, the term herein also includes polypeptides that develop bioactivity after such administration.

In many embodiments of the invention the polypeptide is administered in chemically uncombined form. Many other embodiments are advantageously carried out using the polypeptide in a form (e.g. chemically combined with another substance) in which it has substantially lower solubility in aqueous (e.g. animal body) fluids than the uncombined polypeptide. For example, the polypeptide can be predominantly (e.g. fully) chemically associated with a non-toxic metal or in an ester, amide or other form(s) which provide the desired bioactivity and do not impart intolerable side effects. When chemically associated with such a metal, the metal can be present as the metal per se (e.g. in a metal salt of or complex with the polypeptide) or in the form of a salt or complex of the metal with one or more other anions.

Although monovalent metals (e.g. sodium or potassium) can be used advantageously in some compositions of this invention, polyvalent metals are preferred for use in many other instances. Examples of such polyvalent metals include zinc, iron, calcium, bismuth, barium, magnesium, manganese, aluminum, copper, cobalt, nickel, cadmium and the like. In certain highly preferred embodiments, such metal-associated polypeptides are reaction products of such metals, e.g. in ionic form, with dissolved polypeptides. The ratio of metal to polypeptide may vary depending on the number of active sites of the polypeptide that associate with such metal during the formation process. For instance, metal may be associated with some or all negatively-charged amino acid (e.g. aspartic or glutamic) residues in the polypeptide, or its carboxy terminus. Some or all of the metal may be associated in a salt of the polypeptide, occluded within folds, crystals or amorphous shapes of the polypeptide, or associated as a cation bridge between at least two polypeptide molecules.

When the metal is polyvalent, its valence may be only partly chemically associated with the polypeptide in some cases, e.g. because of steric hindrance. In such cases, the remaining valence of the metal may be chemically associated with other anions. In many desirable embodiments, the metal is not chemically associated in substantial proportion with other anions that form salts having low water solubility with said metal. When the metal is partly chemically associated with other anions, such other anions (organic or inorganic) are often desirably selected from those that form water-soluble salts with that metal, e.g. $Br^-$, $Cl^-$, $I^-$, $SO_4^=$ or $CH_3COO^-$ when the metal is zinc. Monovalent anions, e.g. $Cl^-$, are generally most preferred.

Novel and preferred metal-associated polypeptides of this invention include somatotropins associated with zinc. In some instances, these may contain up to about 5% zinc or more, based on the weight of the somatotropin. To minimize the chance of undesirable injection site responses in the animals, however, it may be desirable for them to contain no more than about 2%, and in some instances no more than about 1% zinc (same basis). In many preferred embodiments these polypeptides contain at least about 0.3% (usually at least about 0.5%) zinc (same basis), although lower percentages of zinc may be suitable in some cases.

Examples of other polypeptide salts useful in this invention include (a) acid addition salts formed with inorganic acids, e.g. hydrochloric, hydrobromic, sulfuric, phosphoric or nitric; or organic acids, e.g. acetic, oxalic, tartaric, succinic, maleic, fumaric, gluconic, citric, malic, ascorbic, benzoic, tannic, pamoic, alginic, polyglutamic, naphthalenesulfonic, naphthalene-disulfonic or polygalacturonic; (b) salts with polyvalent organic cations, e.g. N'-dibenzylethylenediamine or ethylenediamine; and (c) combinations of two or more of the aforementioned types of salts, e.g. zinc tannate.

Preferred are salts of zinc, iron, calcium, magnesium, manganese, sodium, potassium and mixtures thereof. The most preferred salts, especially when the polypeptide is a somatotropin, are those of zinc, sodium or potassium. Very advantageously, it has been found that such salts, when administered in a biocompatible oil in the proportions employed in compositions of this invention, interact with the oil resulting in a matrix or other structure that, surprisingly, enhances prolongation of the polypeptide release at effective levels. This unexpected discovery has been noted in both subcutaneous and intramuscular administrations, and it appears to contribute importantly to the efficacy of many compositions of this invention.

Compositions of this invention are also useful for prolonged release of conjugated or unconjugated polypeptides. Such conjugated polypeptides include lipoproteins, e.g. beta lipoprotein; glycoproteins, e.g. gamma globulin; phosphoproteins, e.g. casein; hemoproteins, e.g. hemoglobin; flavo proteins, e.g. succinate dehydrogenase; and metalloproteins, e.g. ferritin and alcohol dehydrogenase. Mixtures of these or any other of the aforementioned forms of the polypeptide are to be considered within the invention as described and claimed herein.

In many attractive embodiments, the polypeptides administered in compositions of this invention are only slightly water-soluble (i.e., at least 100 parts of room-temperature water required to dissolve one part of polypeptide). In many desirable embodiments they are not very soluble in the biocompatible oil used therein, i.e., not soluble in the biocompatible oil used therein, i.e., not soluble therein at room temperature at a concentration greater than about 2%, and most desirably not greater than about 1%. In some instances, e.g. compositions containing various somatotropins, the polypeptide is both slightly water-soluble and essentially insoluble in the oil.

As aforesaid, the compositions of this invention each contain, as a continuous phase thereof, a biocompatible oil, i.e., an oil having no intolerable adverse effect on the polypeptide, the animal, or, in the case of animals whose products enter the food chain, the consumers of such products. Preferably such oils are of low acidity and essentially free from rancidity. As used herein, the term "oil" means a fatty oil or fat that is liquid at the body temperature of the animal. Thus, such an oil will melt or at least being to melt below about 40° and preferably below about 35°. Oils that are liquid at about 25° may facilitate injection or other administration of some compositions of this invention. In some cases, polyunsaturated (e.g. partially hydrogenated) oils may be favored for greater biocompatibility with the animal or other reasons.

In a preferred embodiment, the biocompatible oil is composed essentially of triglycerides, i.e., long chain (generally $C_8$–$C_{24}$, preferably $C_{12}$–$C_{18}$) fatty acid esters of glycerol, or mixtures of triglycerides and such fatty acids (preferably in only minor proportions, e.g. less than about 10% free fatty acid). In some embodiments, other trihydroxy or polyhydroxy compounds or even monohydroxy compounds (e.g. isopropanol) can be substituted for the glycerol. Especially preferred oils include vegetable oils such as olive, sesame seed, peanut, sunflower seed, soybean, cottonseed, corn, safflower, palm, rapeseed and mixtures of such oils. Sesame and peanut oils are highly preferred for many embodiments. Oils of animal or mineral origin or synthetic oils (including long chain fatty acid esters of glycerol or propylene glycol) can also be employed provided they are sufficiently biocompatible.

In most embodiments such an oil constitutes a predominant part by weight of such compositions. The continuous phase of biocompatible oil has in most cases desirably finely divided, discrete particles of the polypeptide relatively uniformly dispersed therein, e.g. in a suspension. The upper limit of loading of the polypeptide is where the oil ceases to exist in a continuous phase because there is insufficient oil to fully envelop substantially all of the polypeptide in the composition.

I have found surprising and unexpected results by using high loadings of polypeptide in such compositions even when viscosity is thereby substantially increased. Moreover at such high loadings I have discovered an interaction between the polypeptide and oil that in many cases favors a prolonged release of polypeptide from a long-lasting depot. This interaction is enhanced in many cases, as aforesaid, when the polypeptide is associated with a metal.

Thus, compositions of this invention contain a polypeptide at desirably high loading levels, for instance at least about 10%. Even higher loadings of polypeptide, e.g. at least about 15%, are often desirable and especially efficacious with the somatotropins and other polypeptides having substantially similar characteristics. Loadings of about 20% or higher, e.g. at least about 30% or even up to about 50% or higher, can be used advantageously in parenterally injectable compositions comprising a somatotropin (e.g. bovine), in particular when the somatotropin is associated with a polyvalent metal such as zinc. Such compositions can provide prolonged release of the somatotropin (as measured in the blood stream of cattle or other animals) for periods of up to 30 days or longer.

Substantially non-aqueous compositions comprising loading levels of polypeptide as high as about 10% have not been suggested in any prior art of which I am aware. In such prior art oil preparations are restricted to very low loadings of polypeptides, i.e., no more than about 2%. (See U.S. Pat. Nos. 2,964,448; 3,869,549; and 4,256,737.)

Compositions of this invention may also comprise, in addition to the biocompatible oil, an "antihydration agent" which term as used herein means a substance that retards hydration of a given composition of this invention, or the polypeptide and/or biocompatible oil therein, and thereby decreases and/or stabilizes the rate of release of the polypeptide from that composition following administration to an animal. A great variety of non-toxic antihydration agents are known. By way of example there are "gelling" agents which, when dispersed and in some cases heated to dissolve them in the oil, give the body of oil greater viscoelasticity (and therefore greater structural stability) and thereby slow down penetration of the oil by aqueous (e.g. body) fluids.

The exact mechanism of these agents in the present invention is not fully understood. Thus it has been observed that certain known "gelling" agents provide the desired antihydration effect even when the oil containing such an agent has not been heated to enhance their gelling effect, or when the gel formation, once formed, has been substantially eliminated (e.g. by shear forces). Also, various antihydration agents that do not have substantial ability to gel the oil are suitable for use in this invention. Magnesium stearate is one example.

Exemplary antihydration agents include various polyvalent metal salts of organic acids, for instance fatty acids having from about 8 (preferably at least about 10) to about 22 (preferably up to about 20) carbon atoms, e.g. aluminum, zinc, magnesium or calcium salts of lauric acid, palmitic acid, stearic acid and the like. Such salts may be mono-, di-, or tri-substituted, depending on the valence of the metal and the degree of oxidation of the metal by the acid. Particularly useful are the aluminum salts of such fatty acids. Aluminum monostearate and distearate are particularly preferred antihydration agents. Others that are useful include aluminum tristearate, calcium mono- and distearate, magnesium mono- and distearate and the corresponding palmitates, laurates and the like. In many embodiments, the concentration of such an antihydration agent, based on the weight of the oil plus that agent, will be advantageously between about 1% and about 10% (most typically between about 2% and about 5%), although other concentrations may be suitable in some cases.

In general, both the polypeptides and the antihydration agents tend to increase viscosity of the compositions of this invention. With many polypeptides, especially those of relatively high MW and/or complex secondary or tertiary structure, this presents a problem which I have discovered may be overcome by using a weight ratio of polypeptide to antihydration agent that is relatively high. In this invention that ratio is generally at least about 1, more typically at least about 3, even more typically at least about 4, and most commonly at least about 6. Although usually less critical in terms of composition viscosity, that ratio is generally not greater than about 40 and more typically not greater than about 20.

Using such proportions, I have discovered that, even with the higher composition viscosities inherent in relatively high polypeptide concentrations, advantageously long and effective release of the polypeptide is obtained. Even more surprising is the fact that in some of such compositions, the release rate actually increases as polypeptide loading (and therefore composition viscosity) is increased.

The compositions of this invention can be used for prolonged release of polypeptides in animals, especially mammals, including humans and other primates. Useful polypeptides for treating such animals include, e.g., avian hormones for treating chickens, turkeys and the like, mammalian hormones for treating humans, cattle, swine, sheep, goats and the like, and aquatic animal hormones for treating fish and the like. Especially useful polypeptides include growth promoting hormones and lactation enhancing hormones. Such hormones include somatotropins useful for enhancing lean-to-fat ratio, feed efficiency and milk production in various mammalian species including cattle (e.g., dairy cows), sheep, goats and swine.

Polypeptides for which this invention is particularly useful include bovine, ovine and porcine somatotropins, e.g. natural or microbially expressed bovine, ovine and porcine somatotropins, and bovine, porcine or other animal prolactins, growth hormone releasing factors, placental lactogens, insulin-like growth factors and the like.

As used herein the term "somatotropin" means a polypeptide that has biological activity and chemical structure substantially similar to those of a somatotropin produced in the pituitary gland of an animal. Such somatotropins include natural somatotropins produced by pituitary somatotropic cells, and alternatively somatotropins expressed by genetically transformed microorganisms such as E. coli, other bacteria or yeasts. Such alternatively produced somatotropins may have an amino acid sequence identical to the natural somatotropin or may be analogs having one or more variations in amino acid sequence which may provide enhanced biological activity or some other advantage. More particularly, bovine somatotropin can comprise one or more of the polypeptides of the following amino acid sequences:

| | | |
|---|---|---|
| $NH_2$-met-phe(1)-pro(2) | leu(126) | phe(190)-COOH |
| $NH_2$-met-phe(1)-pro(2) | val(126) | phe(190)-COOH |
| $NH_2$-ala-phe(1)-pro(2) | val(126) | phe(190)-COOH |
| $NH_2$-ala-phe(1)-pro(2) | leu(126) | phe(190)-COOH |
| $NH_2$-phe(1)-pro(2) | leu(126) | phe(190)-COOH |
| $NH_2$-phe(1)-pro(2) | val(126) | phe(190)-COOH |
| $NH_2$-met-asp-glu-phe(1)-pro(2) | leu(126) | phe(190)-COOH |
| $NH_2$-met-asp-glu-phe(1)-pro(2) | val(126) | phe(190)-COOH |
| $NH_2$-met(4) | leu(126) | phe(190)-COOH |
| $NH_2$-met(4) | val(126) | phe(190)-COOH |

Polypeptides, such as the above-described somatotropins, optionally have a methionine residue at the N-terminus, e.g. a methionine resulting from microbial translation of an ATG start signal in a gene for the polypeptide. However, in some cases it may be desirable that such methionine residues in the polypeptide are no more than about 20% (preferably no more than about 10%) formyl-methionine, to lessen any tendency of the animal's foreign body defenses to degrade the polypeptide.

Observations of injections of compositions of this invention indicate that a substantial amount of polypeptide is in some cases released initially upon injections. This is referred to as a "burst" which is believed to result from a surface area increase occasioned by injection or other administration. In some cases a modest burst may be desirable, e.g. to activate a desired biological effect. A characteristic useful in formulating compositions of this invention is the relationship of initial burst level determined by measuring the concentration of polypeptide in serum of the treated animal shortly after administration, to the prolonged release level determined by measuring the concentration of polypeptide in serum of the animal at a later time. For purposes of this invention, the burst level is the concentration of the polypeptide in serum 24 hours after injection, and the prolonged release level is the concentration of the polypeptide in serum 14 days after injection. These concentrations are used to calculate a "burst-to-prolonged-release" ratio which is considered generally advantageous between about 1.2 and about 6, say between about 1.5 and about 3.

Another useful characteristic in evaluating and formulating compositions of this invention is "syringeability", a measure of how well the composition flows through a hypodermic injection needle. If particles of the polypeptide are too large or the composition is too viscous, it may require an inordinate pressure to force the composition through such a needle. For purposes of this invention "syringeability" is determined by measuring the time for a volume of a composition of this invention to pass through an 18 gauge hypodermic needle having an I.D. of 0.033 inches (0.838 mm) and a length of 4 cm when a pressure of 173 psi (1193 kPa) is applied to the composition in a syringe fitted with the needle. "Syringeability" for compositions of this invention is desirably at least 0.03 milliliters per second (ml/sec). Preferably such syringeability is higher, e.g. at least about 0.1 ml/sec or, even more desirably, at least about 0.3 ml/sec.

Compositions of this invention can be prepared by adding polypeptide to oil alone or to oil having an antihydration agent suspended or dissolved in the oil. It is often convenient to dissolve an antihydration agent to provide a gelled oil. When compositions of this invention are prepared by a process begun by forming a gelled oil, a gelling agent such as a fatty acid salt of aluminum can be added as a powder to a quantity of oil stirred to effect a suspension of that powder. The stirred suspension may be desirably heated to at least the melting point of the fatty acid salt (e.g. at least 155° for AlMS) at which point the salt will dissolve in the oil. Lower temperatures can be used if the gelling or other antihydration agent is adequately dissolved. Thorough and continuous stirring helps avoid agglomeration of the fatty acid salt and maintain the dispersion. Usually, the heating and stirring should continue until the suspended salt is fully dissolved. It is often desirable to maintain stirring for additional time to assure complete dissolution.

The oil solution of fatty acid salt can then be cooled, e.g. to room temperature, where a fairly stable gel structure will result. The gel should be kept under vacuum or desiccant to avoid contamination with water which may adversely affect the gel structure.

The polypeptide can then be added to the oil at any temperature (e.g. room) that avoids intolerably adverse effects (e.g. denaturing). For instance, bovine somatotropin has been added to such an oil at temperatures from about 4° to about 125° without adversely affecting biological activity. This addition of polypeptide is preferably carried out under vacuum to avoid contamination by water or air bubbles. Such addition is desirably carried out by slow addition of finely divided polypeptide to the oil undergoing high-shear mixing to provide uniform dispersion of the polypeptide particles. Size reduction of the polypeptide particles is often desirable and can be accomplished, e.g., by use of a ball mill in which a suspension of the polypeptide is mixed with a quantity of stainless steel balls having diameters of, e.g., 0.3–0.6 cm. This can be advantageously carried out simultaneously with such dispersion in the lower portion of a vessel in which high shear mixing is effected. This is particularly advantageous with highly charged polypeptides that are difficult to reduce in size to particles having a median particle diameter based on volume not greater than about 15 microns (i.e., 50% of the volume of the particles having diameters not greater than about 15 microns). Use of polypeptides of low particle size (e.g. of such a median particle diameter no greater than about 10, preferably no greater than about 5 microns) has been found desirable for enhancing syringeability of compositions of this invention. By operating such a ball mill the polypeptide particles can be conveniently reduced to such a preferred median particle diameter no greater than about 5 microns. Thereafter, the composition of this invention can be recovered from the ball mill by filtration (advantageously under vacuum).

As aforesaid, the compositions of this invention are attractively useful for parenteral administration, e.g. by injection intraperitoneally or, usually more desirably, subcutaneously or intramuscularly. The duration of prolonged release is that period of time during which the polypeptide is delivered at the rate required for the desired biological effect, typically indicated by the concentration of the polypeptide in the animal's circulating blood stream. Depending on the particular polypeptide and biological effect, the period of prolonged release is desirably at least about 7 days. In other cases, it may be at least about 15 days, or more desirably for many applications at least about 30 days, or even at least about 60 days or longer. Thus, in accordance with this invention, compositions comprising bovine somatotropin associated with zinc have been found to provide, for at least about 7 days in the serum of a lactating cow injected with a 2.5 milliliter dose thereof, an average bovine somatotropin concentration of at least about 12 ng/ml, which is highly advantageous for purposes of enhancing milk production and/or feed-to-milk conversion efficiency in cattle. To provide an effective dose of bovine somatotropin for treating dairy cows, e.g. to enhance milk production, a composition containing at least about 300 mg of a zinc-associated somatotropin is desirable to provide such an increased serum level of active bovine somatotropin for at least about 15 days. It is an importantly attractive feature of this invention that the zinc-associated somatotropin is advantageously present in a high enough concentration (e.g. at least about 15%) to permit the use of a conveniently small volume of the composition (e.g. about 10 ml or less, say between about 1 and about 3 ml) for ease of administration.

Other materials can of course be added to the composition provided such materials do not unacceptably inhibit desirably prolonged release of the polypeptide at effective levels. For example, it may be desirable to add an anti-inflammatory or other additive to a composition of this invention to reduce, prevent or counteract the effects of foreign body (e.g. non-allergic) reaction. Such additives can include steroid and/or non-steroid anti-inflammatory agents which preferably are in the composition at a level low enough to avoid any systemic effect but sufficient to be effective in reducing local inflammation.

Preparation of Metal-Associated Biologically Active Polypeptides

Polypeptides associated with polyvalent metal can be prepared by reacting the dissolved polypeptide with non-toxic metal (e.g. zinc) ions. Generally the metal-associated polypeptide is prepared by adding the metal, optionally in the form of a low water-solubility salt thereof, but generally preferably as a water-soluble salt thereof (e.g. zinc chloride) to a buffered solution of the polypeptide to precipitate the polypeptide associated with the metal.

Often organic solubilizing compounds, e.g. urea, guanidine or the like, are included in the solutions to assist in dissolving the polypeptide, especially for polypeptides that are only slightly water-soluble. In many cases the concentration of solubilizing compound and/or pH of the solution may be critical in maintaining a bioactive conformation of the polypeptide.

Moreover, the pH of the solution is generally critical to recovery of the resulting metal-associated polypeptide, generally as a precipitate. There may be critical ranges of pH depending, e.g., on isoelectric properties of the polypeptide. Temperatures are preferably kept low, e.g. generally no higher than about room temperature, to avoid denaturing.

Depending on purity of the polypeptide to be utilized, depyrogenation and/or sterilization may be desirable. Pyrogens (e.g. endotoxins), if present, can be removed by contacting the polypeptide solution with ion-exchange resin. Most pyrogens will bond to positively charged sites, e.g. on a cation exchange resin. Some pyrogens may bind to negatively charged sites. Accordingly, a mixed bed of ion-exchange resin beads is useful in ensuring sufficient removal of pyrogens. The polypeptide solution can be sterilized to remove non-sterile foreign bodies such as bacteria or loose contaminates from earlier processing by filtration through a fine filter, e.g. 0.2 micron mesh.

The depyrogenated, sterilized polypeptide solution is then contacted with a non-toxic metal solution to precipitate the metal-associated polypeptide, usually desirably forming a suspension. The rate of metal addition affects particle size of the resulting metal-associated polypeptide. Metal addition can be controlled by adjusting metal concentration in the solution added, volumetric flow rate and/or dispersion rate.

Usually, the suspension of metal-associated polypeptide can be diluted to reduce the tendency to increase particle size, e.g. by agglomeration. The metal-associated polypeptide can then be recovered by multiple centrifuging and washing to remove excess metal and anions, followed by lyophilization.

Polypeptides associated with a monovalent metal (e.g. sodium or potassium) can be prepared by lyophilization of a solution of the polypeptide and the metal ion.

Preparation of Metal-Associated Biologically Active Somatotropins

In a more specific illustration of the procedure just described, a somatotropin (e.g. bovine) can be dissolved in a variety of buffered solutions. Preferably it is dissolved in an aqueous urea solution buffered with tris(hydroxymethyl) amino methane (TRIS) or other suitable buffering agent. A desirable upper limit of urea concentration is usually about 6M; in some cases a urea concentration of about 4.5M is preferred. Lower urea concentrations, say 3M or as low as 2M or even 1M, can be used but with lower solubility of the somatotropin.

The pH of the buffered urea solution is preferably between about 7 and about 10.5. Between these pH limits the recovery of somatotropin precipitated from solution is typically at least about 60%. Generally, higher recovery (e.g. at least 90%) can be achieved with a pH between about 9 and about 9.5.

The temperature of the solution throughout the precipitation should be sufficiently low to prevent oligomerization of the somatotropin. Generally such temperatures are desirably lower than about 10° and more preferably lower than about 5°.

To provide a monovalent metal-associated polypeptide, the solution (depyrogenated and sterilized as aforesaid) is treated by diafiltration (or dialysis) to exchange the urea with a solution of the metal bicarbonate (e.g. a 25 mM NaHCO$_3$ solution, pH 9.5) or other suitable salt. Multiple exchanges with the bicarbonate solution are preferably conducted to ensure complete exchange of urea. The solution is then treated by further diafiltration with water to remove excess NaHCO$_3$ which is indicated by the start of precipitation of MBS. Recovery of sodium-somatotropin by lyophilization produces a powder of the sodium salt of the somatotropin.

To provide a polyvalent metal-associated polypeptide, the solution (depyrogenated and sterilized as aforesaid) is contacted with a polyvalent (e.g. zinc) salt. Use of a 1M solution of zinc chloride has been found to produce acceptable precipitated zinc-somatotropin from 4.5M urea solution of the somatotropin, although higher or lower concentrations of the chloride can be utilized. The ZnCl$_2$ solution is preferably added slowly, e.g. as by titration, while stirring the somatotropin solution.

As addition of the ZnCl$_2$ solution is continued, the somatotropin solution reaches first an off-white, then pearly-white color as the stoichiometric amount of ZnCl$_2$ is added. For instance, by adding 4 ml of 1M ZnCl$_2$ to 400 ml of a pH 9.5 solution containing about 20 mg somatotropin per ml and 0.09M TRIS in 4.5M urea, a uniform, pearly-white zinc-somatotropin suspension will be formed. Additional ZnCl$_2$ (e.g. up to about 10 ml of 1M ZnCl$_2$ solution) can be added to ensure complete precipitation.

The suspension is then often desirably diluted to reduce the tendency to increase particle size of the precipitate. Dilution with up to about 3.5 volumes of water to about 1M urea has been found satisfactory to keep the zinc-somatotropin particles from agglomerating. Recovery by diafiltration (or multiple centrifuging and washing) to remove urea, TRIS and zinc and chlorine ions, followed by lyophilization, produces a powder having particle sizes generally less than between 10 and 20 microns.

When the somatotropin is bovine, the particles typically contain between about 0.3 and about 1% zinc (between about 1 and 4 molecules of zinc per molecule of somatotropin). If zinc addition rate is increased, higher amounts are found in the precipitate, e.g. up to 4–5%. Such higher amounts may be due to additional binding of zinc to active acid sites on the somatotropin, e.g. at additional aspartic and/or glutamic acid residues or possibly at histidine residues, or at the carboxy terminus of the polypeptide. It is not intended that this theory of zinc binding be considered limiting to the scope of this invention. In general, precipitation using an essentially minimum amount of zinc is considered preferable.

The following disclosure is provided to illustrate specific embodiments and aspects of this invention but does not imply any limitation of the scope of the invention.

EXAMPLE 1

This example illustrates the preparation of a zinc-associated bovine somatotropin of this invention.

Methionine N-terminated bovine somatotropin (MBS) was prepared as described by Seeburg, et al. in "Efficient Bacterial Expression of Bovine and Porcine Growth Hormone", 2(1) *DNA* 37–45 (1983), incorporated herein by reference. The somatotropin was recovered in useful form by lysing the bacterial cells and then separating the somatotropin from bacterial cell debris.

In one method of recovering MBS the bacteria were killed by treatment with 50% sulfuric acid sufficient to lower pH of the fermentation broth to 1.7. The broth was neutralized with NaOH and centrifuged, leaving a cell paste which was suspended in urea, homogenized, cooled to about 4° C. (that temperature was maintained until the MBS lyophilization referred to below), centrifuged and washed three times, dissolved in guanidine hydrochloride (7M), centifuged to remove insolubles, filtered, passed through a G25 Sephadex column in which the guanidine was exchanged for urea, filtered and then passed through a DE52 ion exchange column. The volume of the effluent was reduced about 30X by hollow fiber ultrafiltration. The concentrated solution was passed through a G75 Sephadex chromatography column, another hollow fiber volume reduction step and then dialyzed to exchange the urea first for $NaHCO_3$ solution and then distilled water to precipitate the MBS. The precipitate was lyophilized, leaving a white solid (slightly soluble in water) containing a polypeptide (MBS) having the $NH_2$-met-phe(1)-pro(2) ... leu(126) ... phe(190)-COOH amino acid sequence expressed in the aforementioned publication by Seeburg et al.

Such MBS was dissolved in a 4.5M urea, 0.09M TRIS solution at 21.5 mg MBS per ml, 4° and pH 9.5. The MBS solution was depyrogenated by mixing with 0.2 grams of mixed anionic/cationic ion exchange resin beads (Biorad AG-501X8) for each ml of sterile MBS solution. The mixture was stirred for about 10 minutes at 4° and then filtered with a 1 micron nylon filter to remove the beads containing adsorbed pyrogens.

The depyrogenated MBS was sterilized by passing the solution through a radiation sterilized, pleated capsule filter having 0.2 micron mesh to remove non-sterile foreign bodies such as bacteria or loose contaminates from earlier processing.

The MBS was converted to a zinc salt (ZnMBS) by adding 1M $ZnCl_2$ while stirring the depyrogenated MBS solution. The precipitated ZnMBS contained approximately 1% zinc. The solution containing ZnMBS solids was then diluted with sterile depyrogenated water to an urea concentration of 1M.

ZnMBS was recovered by centrifuging at 10,000×g for 30 min. while maintaining the solution at 4°. The ZnMBS was suspended in sterile depyrogenated water at 50 mg ZnMBS/ml using high shear mixing. ZnMBS was again recovered by centrifuging at 10,000×g for 30 min, resuspended in sterile depyrogenated water at 50 mg ZnMBS/ml using high shear mixing, and then lyophilized to produce a white fluffy powder of sterile ZnMBS.

EXAMPLE 1A

This example illustrates an alternative preparation of ZnMBS.

A depyrogenated and sterilized solution of 21 mg of MBS per ml in 4.5M urea, 0.05M TRIS, 10° and pH 8.8 was recirculated through a hold tank by a positive displacement pump. 1M $ZnCl_2$ was added at the pump suction until the concentration of the solution was 0.01M $ZnCl_2$ resulting in precipitation of ZnMBS. Dilution water was added to provide a concentration of 10 mg MBS per ml resulting in further precipitation of ZnMBS. The resulting suspension of ZnMBS was then circulated at 25° through a diafiltration hollow fiber membrane, having pores which would pass molecules of up to 100,000 MW, until the concentration reached 40 mg MBS per ml; then water was added to match the membrane filtrate rate until essentially all of the Zn, urea and TRIS was removed from the suspension. Water addition was stopped to allow concentration to about 80 mg MBS per ml. The concentrated suspension was then lyophilized to provide a dry, white powder of ZnMBS having particle sizes in the range of 0.5 to 11 microns.

EXAMPLE 1B

This example illustrates the preparation of a sodium-associated bovine somatotropin.

A depyrogenated and sterilized solution of 21.5 mg per ml in 4.5M urea, 0.05M TRIS, 4° and pH 9.5 was dialyzed to exchange urea first for $NaHCO_3$ solution and then distilled water. The water exchange was stopped when the MBS begins to precipitate. The solution was then filtered with a 0.2 micron filter to remove precipitated MBS and lyophilized to provide a sodium salt (NaMBS) which can be used in compositions of this invention.

EXAMPLE 2

This example illustrates the preparation of a composition of this invention containing a zinc-associated somatotropin.

A volume of sesame oil (Fisher NF Grade) was added to a three-necked round bottom flask. An antihydration agent (AlMS) at 5% of total AlMS and sesame oil was added. The flask was placed in an oil bath at 155° and stirred to disperse the AlMS as rapidly as possible. Stirring continued for 20 minutes, during which the AlMS dissolved completely in the oil. The flask was removed from the bath, kept under vacuum and allowed to cool to 25°. On cooling, the solution converted to a thick gel. The cooled gel was fed into a ball mill having a high-shear agitator in a bed of stainless steel balls having ⅛, 3/16 and ¼ inch (0.32, 0.48 and 0.64 cm) diameters. Vacuum was applied to the mill and ZnMBS powder (prepared as described in Example 1) was slowly added using a screw feeder until the composition contained 40% ZnMBS (13.3 wt. ratio of ZnMBS to AlMS). Stirring was continued for 6 hours during which the median particle diameter of the ZnMBS was reduced from 20 microns to 5 microns. The resulting substantially non-aqueous gelled oil suspension of ZnMBS was separated from the steel balls by filtration.

EXAMPLE 3

This example illustrates an efficacious use of a composition of this invention in prolonged release of a polypeptide, i.e. a bovine somatotropin, to enhance milk production in lactating dairy cattle.

A substantially non-aqueous composition was prepared essentially as in Example 2 by dissolving 5% AlMS in sesame oil heated to 155° C. The oil was cooled to form a gelled oil. ZnMBS was dispersed and milled in the oil until the composition contained 32% ZnMBS in a continuous phase of the oil (9.4 wt. ratio of ZnMBS to AlMS). Syringes equipped with 18 gauge, 1.5 inch (3.8 cm) long needles were loaded with 2.54 grams (2.5 ml) of composition to provide a dose containing 805 mg ZnMBS. The composition had a syringeability of 0.36 ml/sec. Blank compositions of 5% AlMS in sesame oil without the polypeptide were also prepared and loaded at 2.4 grams into identical syringes.

The compositions were injected into 23 Holstein dairy cattle in the second or third trimester of their second (or subsequent) lactation. The cattle were randomly organized into 4 groups of 5 or 6. Two groups were injected intramuscularly (IM) in the gluteal region, one with the ZnMBS-containing composition and the other (a control group) with the blank composition. Similarly, two other groups were injected subcutaneously (SQ) in the suprascapular region with the ZnMBS-containing or blank composition.

Cumulative least-square means for average milk production (covariantly adjusted for differences in pretreatment milk yields) are shown in Table 1, where milk production is expressed in kilograms of milk per day. As shown in Table 1, a single IM or SQ injection of a conveniently-administered composition of this invention provides a rapid and prolonged improvement in milk production at very high levels of statistical significance.

Antihydration agent: AlMS at 3% or 5% of oil plus AlMS.
Polypeptide loading: ZnMBS at 20%, 30% or 40% of total composition.

The AlMS was dispersed in the oil. The dispersion, after being heated to and maintained at 155° for 15 minutes, was

TABLE 1

CUMULATIVE ADJUSTED AVERAGE DAILY MILK PRODUCTION (MP), KG/DAY

| | | 7 days | | 14 days | | 21 days | | 30 days | |
|---|---|---|---|---|---|---|---|---|---|
| Dose | Route | MP | % Ctrl (a) | MP | % Ctrl | MP | % Ctrl | MP | % Ctrl |
| Control | IM | 23.3 | — | 22.4 | — | 22.0 | — | 21.1 | — |
| ZnMBS | IM | 26.6 | 16.2 | 26.0 | 17.1 | 24.9 | 13.7 | 22.9 | 9.6 |
| Control | SQ | 22.5 | — | 21.1 | — | 21.8 | — | 20.6 | — |
| ZnMBS | SQ | 25.1 | 9.6 | 24.8 | 11.7 | 24.0 | 9.6 | 22.1 | 5.7 |
| Combined IM and SQ | | | | | | | | | |
| (1) Control | | 22.9 | — | 22.2 | — | 21.9 | — | 20.9 | — |
| (2) ZnMBS | | 25.9 | 13.1 | 25.4 | 14.4 | 24.4 | 11.4 | 22.6 | 8.1 |
| Contrast | | | | | Significance Levels | | | | |
| (2) vs. (1) | | .0001 | | .0001 | | .0004 | | .0187 | |

(a) % Ctrl represents percent improvement relative to average control response.

Blood samples were analyzed for bovine somatotropin which, without administration in accordance with this invention, is normally present in the circulatory systems of cattle. Representative analyses by radioimmunoassay ("RIA") are shown in Table 2 where the concentrations of bovine somatotropin in blood serum are expressed in nanograms per milliliter (ng/ml).

TABLE 2

Average Plasma Concentration of Bovine Somatotropin, ng/ml

| Days After Injection | Intramuscular | | Subcutaneous | |
|---|---|---|---|---|
| | Control | ZnMBS | Control | ZnMBS |
| 0 | 6.7 | 5.9 | 5.1 | 5.7 |
| 1 | 6.5 | 8.4 | 4.6 | 8.7 |
| 2 | 7.8 | 9.0 | 4.3 | 11.1 |
| 3 | 7.1 | 9.1 | 4.0 | 10.1 |
| 4 | 7.5 | 10.1 | 4.5 | 9.8 |
| 5 | 8.1 | 12.0 | 3.1 | 11.2 |
| 6 | 8.1 | 18.2 | 3.9 | 11.9 |
| 7 | 8.0 | 21.2 | 3.6 | 12.9 |
| 9 | 7.9 | 21.3 | 6.6 | 16.5 |
| 11 | 6.8 | 18.2 | 5.2 | 16.6 |
| 13 | 7.6 | 16.7 | 5.2 | 17.5 |
| 15 | 7.0 | 16.2 | 5.4 | 15.7 |
| 17 | 5.6 | 12.9 | 4.1 | 11.7 |
| 19 | 5.4 | 13.8 | 4.4 | 12.0 |
| 21 | 6.0 | 11.2 | 4.3 | 10.0 |
| 23 | 5.7 | 10.6 | 5.3 | 9.5 |
| 25 | 5.6 | 9.8 | 4.4 | 9.0 |
| 27 | 5.8 | 8.4 | 4.9 | 8.5 |
| 29 | 3.5 | 6.8 | 1.1 | 7.4 |
| 31 | 3.8 | 5.9 | 2.5 | 6.7 |

EXAMPLE 4

This example illustrates the efficacy of compositions of this invention for prolonged release of a polypeptide (MBS) in animals using a variety of materials in such compositions.

In this example, ZnMBS compositions were formulated essentially as disclosed in Example 3 using combinations of the following constituents:

Biocompatible oil: Sesame seed or peanut.

allowed to cool to 25°, forming a gelled oil. ZnMBS was added and dispersed by a high shear mixer (Polytron Homogenizer) forming a suspension of ZnMBS in the gelled oil. The suspension was loaded into tuberculin syringes having 18 gauge hypodermic needles.

By subcutaneous injection at the dorsal suprascapular region, the compositions listed in Table 3 were administered to 16 groups of 8 immunosuppressed female Sprague-Dawly (IFS-D) rats.

TABLE 3

Injected Compositions

| Group | Dose Volume, Microliters | Oil | AlMS, %(a) | ZnMBS, % | Wt. Ratio, ZnMBS/AlMS |
|---|---|---|---|---|---|
| 1 | 200 | sesame | 3 | none | — |
| 2 | 200 | sesame | 3 | 20 | 8.3 |
| 3 | 130 | sesame | 3 | 30 | 14.3 |
| 4 | 100 | sesame | 3 | 40 | 22.2 |
| 5 | 200 | sesame | 5 | none | — |
| 6 | 200 | sesame | 5 | 20 | 5.0 |
| 7 | 130 | sesame | 5 | 30 | 8.6 |
| 8 | 100 | sesame | 5 | 40 | 13.3 |
| 9 | 200 | peanut | 3 | none | — |
| 10 | 200 | peanut | 3 | 20 | 8.3 |
| 11 | 130 | peanut | 3 | 30 | 14.3 |
| 12 | 100 | peanut | 3 | 40 | 22.2 |
| 13 | 200 | peanut | 5 | none | — |
| 14 | 200 | peanut | 5 | 20 | 5.0 |
| 15 | 130 | peanut | 5 | 30 | 8.6 |
| 16 | 100 | peanut | 5 | 40 | 13.3 |

(a)Based on weight of oil plus AlMS.

Blood samples were analyzed by RIA for bovine somatotropin. Analyses in Table 4 are in ng/ml of blood plasma. Such plasma levels are shown in Table 4 for blood samples taken prior to injection on day 0 (the injection day). Some baseline measurements for rats in Examples 4–7 are higher than some baseline and released polypeptide measurements for cows in Example 3. This is partly because of interspecies differences in normal somatotropin levels and partly because the RIA in Example 3 was more precise).

TABLE 4

Average Plasma Concentration of Bovine Somatotropin, ng/ml

| | Days After Injection | | | | | | | | |
|---|---|---|---|---|---|---|---|---|---|
| Group | 0 | 1 | 3 | 7 | 11 | 14 | 21 | 28 | 35 |
| 2 | 9 | 765 | 440 | 304 | 138 | 83 | 21 | 18 | 22 |
| 3 | 10 | 494 | 309 | 237 | 141 | 113 | 60 | 31 | 15 |
| 4 | 6 | 381 | 245 | 239 | 169 | 136 | 49 | 35 | 62 |
| 6 | 11 | 255 | 91 | 146 | 119 | 86 | 49 | 40 | 48 |
| 7 | 6 | 338 | 194 | 181 | 203 | 141 | 83 | 44 | 53 |
| 8 | 6 | 468 | 258 | 151 | 134 | 149 | 103 | 48 | 35 |
| 10 | 6 | 735 | 470 | 255 | 152 | 94 | 32 | 25 | 19 |
| 11 | 6 | 582 | 391 | 221 | 166 | 134 | 47 | 30 | 32 |
| 12 | 11 | 753 | 361 | 224 | 171 | 146 | 72 | 41 | 52 |
| 14 | 7 | 383 | 178 | 143 | 95 | 77 | 41 | 34 | 29 |
| 15 | 8 | 479 | 246 | 183 | 197 | 215 | 106 | 67 | 70 |
| 16 | 7 | 413 | 281 | 146 | 142 | 135 | 66 | 39 | 49 |

(Average concentration readings for Control Groups 1, 5, 9 and 13 were between 5 and 12 ng/ml on each of the days shown above).

EXAMPLE 5

This example illustrates the efficacy of compositions of this invention for prolonged release of a polypeptide (MBS) utilizing other fatty acid salts of aluminum as antihydration agents. In these compositions, aluminum monolaurate (AlML) and aluminum monopalmitate (AlMP) were utilized as antihydration agents with sesame and peanut oils.

In this example, gelled oils containing 3% of AlML or AlMP were prepared essentially as in Example 4. ZnMBS was suspended in the gelled oils at a concentration of 30% of the total composition (14.3 wt. ratio of ZnMBS to AlML or AlMP). Each composition was injected into a group of 8 IFS-D rats at the dosages indicated in Table 5.

TABLE 5

Injected Compositions

| Group | Dose Volume, Microliters | Oil | Antihydration Agent |
|---|---|---|---|
| 17 | 130 | sesame | AlML |
| 18 | 130 | sesame | AlMP |
| 19 | 130 | peanut | AlML |
| 20 | 130 | peanut | AlMP | analyses of blood samples taken from the rats on the indicated days after injection resulted in the concentrations of bovine somatotropin shown in Table 6, where the readings on day 0 are baseline for the analysis.

TABLE 6

Average Bovine Somatotropin Concentrations in Plasma, ng/ml

| | Days After Injection | | | | |
|---|---|---|---|---|---|
| Group | 0 | 1 | 3 | 7 | 14 | 21 |
| 17 | 9 | 431 | 143 | 172 | 49 | 30 |
| 18 | 10 | 632 | 229 | 277 | 58 | 33 |
| 19 | 11 | 421 | 162 | 198 | 32 | 28 |
| 20 | 9 | 492 | 164 | 210 | 17 | 35 |

EXAMPLE 6

This example illustrates the efficacy of compositions of this invention for prolonged release of a polypeptide (MBS) utilizing olive oil or corn oil.

In this example, gelled oils were prepared essentially as in Example 4 utilizing 3% AlMS based on AlMS plus the oil. The suspensions of 30% or 40% ZnMBS were injected into two groups of 8 IFS-D rats at the dosages indicated in Table 7.

TABLE 7

Injected Compositions

| Group | Dose Volume, Microliters | Oil | ZnMBS, % | Wt Ratio ZnMBS/AlMS |
|---|---|---|---|---|
| 21 | 100 | olive | 40 | 22.2 |
| 22 | 130 | corn | 30 | 14.3 |

Analyses of blood samples taken from the rats on the indicated days after injection resulted in the concentrations of bovine somatotropin shown in Table 8, where the readings on day 0 are baseline for the analyses.

TABLE 8

Average Bovine Somatotropin Concentrations in Plasma, ng/ml

| | Days After Injection | | | | |
|---|---|---|---|---|---|
| Group | 0 | 1 | 4 | 11 | 14 | 25 |
| 21 | 7 | 996 | 314 | 174 | 98 | 36 |
| 22 | 7 | 1314 | 444 | 158 | 98 | 35 |

EXAMPLE 7

This example illustrates compositions of this invention comprising about 10% of the polypeptides, MBS and ZnMBS, in peanut oil. This example further illustrates that prolonged effect of the polypeptide can be enhanced by using the polypeptide associated with a metal and by use of an antihydration agent. Compositions as indicated in Table 9 for injection were prepared essentially as in Example 4.

TABLE 9

Injected Compositions

| Group | Polypeptide | Polypeptide Loading, % | Oil | AlMS, %[a] |
|---|---|---|---|---|
| 30 | MBS | 10 | peanut | — |
| 31 | ZnMBS | 10 | peanut | — |
| 32 | MBS | 10 | peanut | 1 |
| 33 | ZnMBS | 10 | peanut | 1 |

[a]Based on weight of oil plus AlMS.

Each composition was injected subcutaneously into a group of 8 IFS-D rats at a dosage of 300 microliters. Analysis of blood samples taken from the rats on the indicated days after injection indicated plasma concentrations as shown in Table 10, where the readings on day 0 are baseline for the analyses.

TABLE 10

| | Average Bovine Somatotropin Concentrations in Plasma, ng/ml | | | | | | |
|---|---|---|---|---|---|---|---|
| | Days After Injection | | | | | | |
| Group | 0 | 1 | 3 | 5 | 7 | 11 | 14 |
| 30 | 14 | 1350 | 375 | 145 | 75 | 50 | 20 |
| 31 | 15 | 1800 | 310 | 240 | 200 | 40 | 20 |
| 32 | 12 | 1200 | 250 | 123 | 64 | 35 | 21 |
| 33 | 18 | 620 | 350 | 330 | 280 | 175 | 125 |

Comparison of the results for Groups 30 and 31 illustrates enhancement of prolonged release of MBS for at least 7 days by use of an associated polyvalent metal. Comparison of the results for Groups 32 and 33 illustrates enhancement of prolonged release of MBS by use of an antihydration agent when the MBS is associated with such a polyvalent metal.

While specific embodiments of the invention have been described, it should be apparent to those skilled in the art that various modifications thereof can be made without departing from the true spirit and scope of the invention. Accordingly, it is intended that the following claims cover all such modifications within the full inventive concept.

I claim:

1. A substantially non-aqueous composition comprising at least about 10% by weight of a biologically-active somatotropin polypeptide and, as a continuous phase of said composition, a biocompatible oil, the composition effective upon administration for forming parenterally in an animal a sustained-release depot releasing somatotropin for a period of at least about seven days.

2. A composition of claim 1 comprising a bovine or porcine somatotropin.

3. A composition of claim 1 comprising at least about 1% by weight of a non-toxic antihydration agent, said polypeptide being present in said composition in a weight ratio to said antihydration agent of at least about 1.

4. A composition of claim 3 wherein the antihydration agent is predominantly a metal salt of a $C_8$–$C_{22}$ fatty acid.

5. A composition of claim 2 wherein the somatotropin polypeptide is chemically associated with a non-toxic metal.

6. A composition of claim 5 wherein the metal is selected from the group consisting of zinc, sodium and potassium.

7. A composition of claim 4 wherein the antihydration agent is predominantly an aluminum or magnesium salt of a $C_8$–$C_{22}$ fatty acid.

8. A composition of claim 1 comprising at least about 15% by weight of a somatotropin.

9. A composition of claim 1 comprising at least about 300 milligrams of somatotropin.

* * * * *